United States Patent [19]

Miller

[11] Patent Number: 5,088,502
[45] Date of Patent: Feb. 18, 1992

[54] SKIN SURFACE SAMPLING AND VISUALIZING DEVICE

[75] Inventor: David L. Miller, Dallas, Tex.

[73] Assignee: Cuderm Corporation, Dallas, Tex.

[21] Appl. No.: 626,635

[22] Filed: Dec. 12, 1990

[51] Int. Cl.⁵ .............................................. A61B 10/00
[52] U.S. Cl. ..................................... 128/759; 604/307
[58] Field of Search ................ 128/749, 759; 604/289, 604/290, 304, 307, 312, 313

[56] References Cited

U.S. PATENT DOCUMENTS

| | | | |
|---|---|---|---|
| 2,969,057 | 1/1961 | Simmons | 128/759 |
| 3,512,518 | 5/1970 | Mishkin et al. | 128/759 |
| 3,965,888 | 6/1976 | Bender | 128/759 |
| 4,532,937 | 8/1985 | Miller | 128/759 |

FOREIGN PATENT DOCUMENTS 2599500 12/1987 France ................ 128/759

Primary Examiner—Max Hindenburg
Attorney, Agent, or Firm—Ross, Howison, Clapp & Korn

[57] ABSTRACT

A device for sampling the surface of the skin includes a substrate having a light absorbing area disposed thereon. A layer of adhesive is disposed on the substrate overlying the light absorbing area. The adhesive layer is optically clear and under pressure conforms to the surface of the skin to be sampled. A removable protective film is disposed on the adhesive layer for protecting the adhesive layer prior to use of the device.

2 Claims, 1 Drawing Sheet

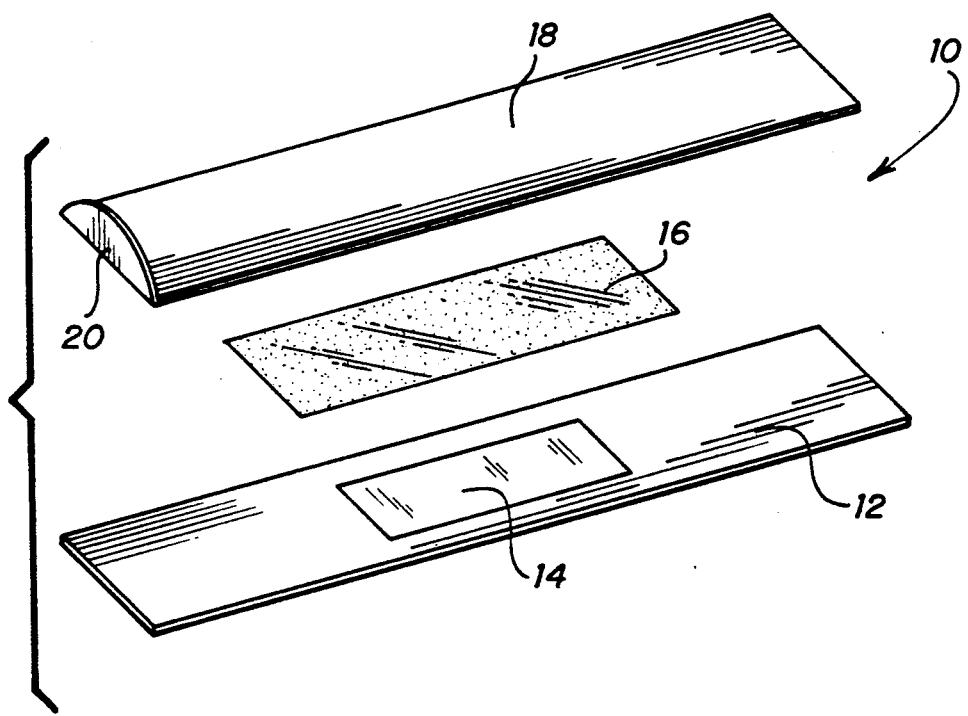

SKIN SURFACE SAMPLING AND VISUALIZING DEVICE

TECHNICAL FIELD OF THE INVENTION

This invention relates to skin sampling devices, and more particularly to a pressure sensitive adhesive device for collecting and visualizing skin cells.

BACKGROUND OF THE INVENTION

For various medical reasons, it is desirable to sample and collect skin cells from the surface of the skin of a subject. Some conditions of dry skin are difficult to observe when looking at the skin on the body. For example, the strength or weakness of intercellular bonds under certain conditions is hard to observe. Therefore, cell collection methods have been proposed for removal of skin cells for subsequent microscopic study.

Skin sampling methods have included scraping the skin with a blade which has the undesirable result of removing well attached skin cells along with loose dead cells and which may result in unwanted cuts to the skin. Brushing and detergent washing filtered on paper is an additional approach that has been used with test results varying upon the scope of the area washed. Adhesive tape with either a black background or clear or translucent background has also been used, but uniformity of test area and repeatability of test is not ascertainable. In addition, liquid adhesives have been applied to the skin, which when dried are peeled off, thereby pulling with the adhesive, debris from the skin and from the skin pores.

A need has arisen for a reliable and easily visible device for skin sampling for the collection of skin cells from the surface of the skin.

SUMMARY OF THE INVENTION

In accordance with the present invention, a device for sampling and visualizing loose cells sampled from the surface of the skin is provided. The device includes a substrate having a light absorbing area disposed thereon. A layer of adhesive is disposed on the substrate overlying the light absorbing area. The adhesive layer is optically clear and under pressure conforms to the surface of the skin to be sampled. A removable protective film is disposed on the adhesive layer for protecting the adhesive layer prior to use of the device.

BRIEF DESCRIPTION OF THE DRAWING

For a more complete understanding of the present invention and for further advantages thereof, reference is now made to the following Description of the Preferred Embodiments taken in conjunction with the accompanying Drawing which is an exploded perspective view of the present device.

DESCRIPTION OF THE PREFERRED EMBODIMENTS

Referring to the Figure, the present device for sampling the surface of skin is illustrated, and is generally identified by the numeral 10. Device 10 includes a substrate 12 such as, for example, a flexible cardboard layer having a thickness of, for example, approximately 1 to 10 mils thick. Disposed on substrate 12 is a light absorbing area 14. Light absorbing area 14 comprises a dark colored area which may be printed on substrate 12 using standard printing techniques.

Disposed on substrate 12 and overlaying area 14 is a layer of adhesive 16. Adhesive layer 16 may have a thickness of from approximately 0.2 mils to 2 mils thick. The adhesive comprising adhesive layer 16 is further described in U.S. Pat. No. 4,532,937, which description is hereby incorporated by reference. Adhesive layer 16 includes adhesive that is aggressive, clear and that under pressure readily flows to conform to the configuration of the skin surface being sampled when substrate 12 with adhesive layer 16 in contact with the skin is pressed against the skin being sampled.

In order to provide protection for adhesive layer 16, a removable protective film 18 is disposed over adhesive layer 16 for preventing unwanted debris from adhering to adhesive layer 16 prior to skin surface sampling. Removable protective film 18 includes a tab 20 to assist in removing film 18 from adhesive layer 16 prior to skin sampling. Protective film 18 may comprise, for example, a thin film of paper, plastic or other material which is easily severable from adhesive layer 16 without removing adhesive layer 16 from substrate 12 when film 18 is removed.

In use of device 10, film 18 is removed from substrate 12 and adhesive layer 16 is placed adjacent to the skin surface to be sampled. Substrate 12 is pressed against the surface of the skin, and when removed, skin cells adhere to adhesive layer 16. Light absorbing area 14 provides a contrasting background in which to visualize the sampled cells in ordinary light and provides a uniform area for analyzing the skin cells removed from the sampled skin surface. The amount and nature of skin surface cells removed is immediately visualized by contrast with, and against the dark colored area 14.

It therefore can be seen that the present skin surface sampling device provides for easy application with repeatable results for uniform testing of skin surfaces. The device is easy to handle by the user prior to skin sampling through the use of a protective film overlaying the adhesive collection film. Further, the present device provides for easy visualization of the skin cells collected.

Whereas the present invention has been described with respect to specific embodiments thereof, it will be understood that various changes and modifications will be suggested to one skilled in the art and it is intended to encompass such changes and modifications as fall within the scope of the appended claims.

I claim:

1. A device for observing the degree of dry skin comprising:
    an opaque, flexible substrate;
    a dark colored light absorbing area printed on said substrate;
    a layer of adhesive disposed on said substrate and overlaying said light absorbing area, said adhesive layer being optically clear and when under pressure comformable to the surface of the skin being observed for transferring dry skin flakes to said substrate in the region of said light absorbing area; and
    a removable protective film disposed on said adhesive layer for protecting said adhesive layer prior to use of the device.

2. The device of claim 1 wherein said protective film includes a tab portion not in contact with said adhesive layer for assisting in removal of said protective film from said adhesive layer.

* * * * *